US006241662B1

(12) United States Patent
Richards-Kortum et al.

(10) Patent No.: US 6,241,662 B1
(45) Date of Patent: Jun. 5, 2001

(54) ACETIC ACID AS A SIGNAL ENHANCING CONTRAST AGENT IN FLUORESCENCE SPECTROSCOPY

(75) Inventors: Rebecca Richards-Kortum; Anant Agrawal; Costas Pitris; Urs Utzinger, all of Austin; Carrie Brookner, Missouri City; Michele Follen Mitchell, Houston, all of TX (US)

(73) Assignee: Lifespex, Inc., Kirkland, WA (US)

( * ) Notice: Subject to any disclaimer, the term of this patent is extended or adjusted under 35 U.S.C. 154(b) by 0 days.

(21) Appl. No.: 09/175,232

(22) Filed: Oct. 20, 1998

Related U.S. Application Data

(60) Provisional application No. 60/076,985, filed on Mar. 5, 1998, and provisional application No. 60/062,922, filed on Oct. 20, 1997.

(51) Int. Cl.$^7$ ............................................ A61B 5/00
(52) U.S. Cl. .................. 600/310; 600/312; 600/317; 600/473; 600/475; 600/477; 356/346; 356/349; 356/432
(58) Field of Search ................... 600/407, 310, 600/312, 317, 473, 475, 476, 477; 356/432, 346, 349

(56) References Cited

U.S. PATENT DOCUMENTS

| 4,556,057 | * | 12/1985 | Hiruma et al. .................. 128/665 |
| 5,697,373 |   | 12/1997 | Richards-Kortum et al. . |
| 5,733,739 | * | 3/1998 | Zakim et al. ..................... 435/29 |
| 5,842,995 |   | 12/1998 | Mahadevan-Jansen et al. . |

* cited by examiner

Primary Examiner—Marvin M. Lateef
Assistant Examiner—Jeoyuh Lin
(74) Attorney, Agent, or Firm—Fish & Richardson P.C.

(57) ABSTRACT

A method for using acetic acid as a signal enhancing contrast agent during fluorescence spectroscopy of normal and neoplastic tissue, particularly epithelium. In one aspect, the invention includes a method of detecting tissue abnormality in a diagnostic tissue sample in a patient, comprising the steps of obtaining a first fluorescence intensity spectrum from the diagnostic tissue sample; thereafter, applying acetic acid to the diagnostic tissue sample in sufficient concentration to alter the response of such diagnostic tissue sample to electromagnetic radiation for at least an effective period of time; during the effective period of time, obtaining a second fluorescence intensity spectrum from the diagnostic tissue sample; determining a parameter indicative of a change between the first and second fluorescence emission intensity spectra; and analyzing the determined parameter to determine a probability that the diagnostic tissue sample is normal or abnormal.

13 Claims, 5 Drawing Sheets

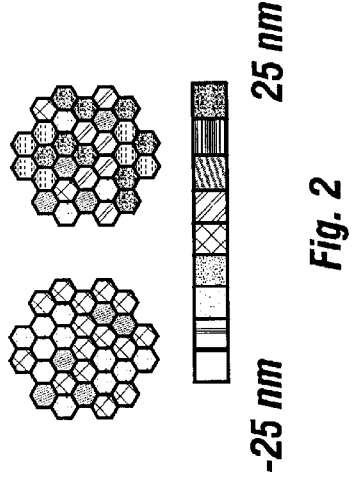
Fig. 2
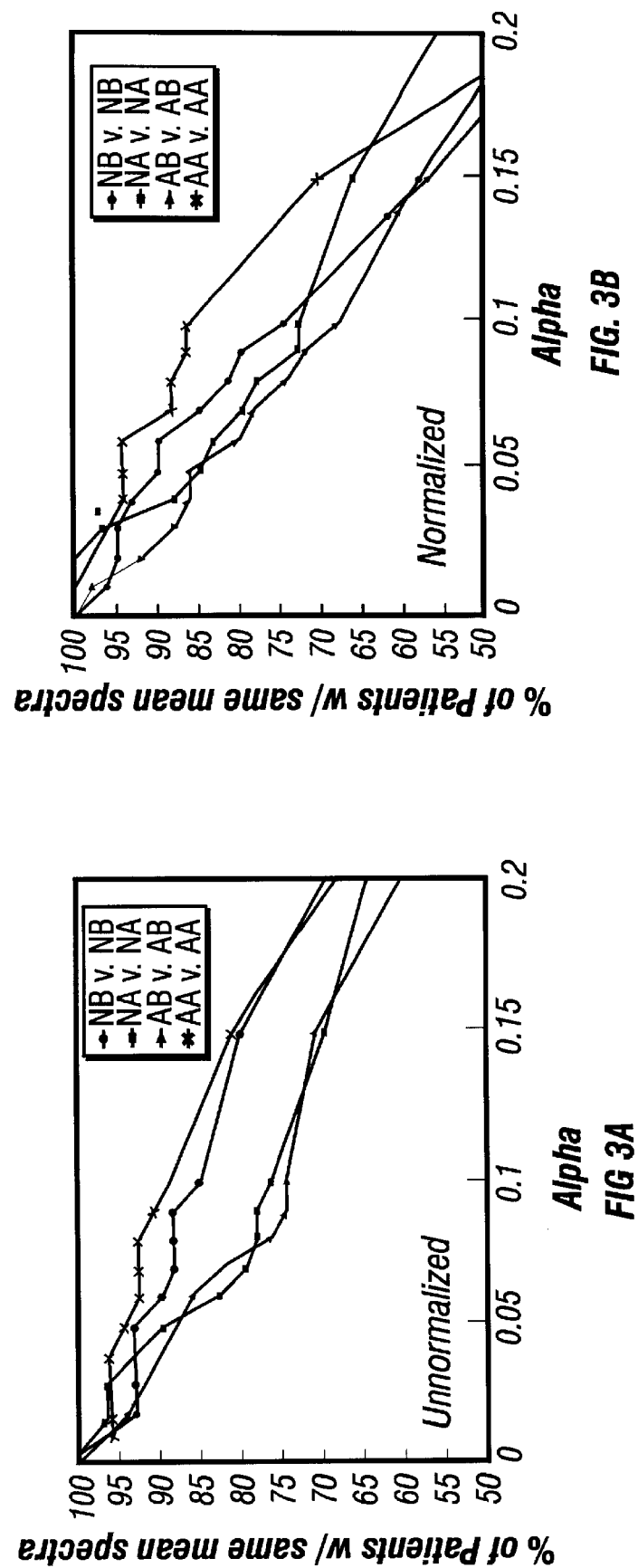
FIG. 3A
FIG. 3B

FIG. 5A

Unnormalized ($\alpha = 0.07$)

FIG. 5B

Normalized ($\alpha = 0.05$)

ACETIC ACID AS A SIGNAL ENHANCING CONTRAST AGENT IN FLUORESCENCE SPECTROSCOPY

CLAIM OF PRIORITY

This application claims priority under 35 USC §119(e) to U.S. patent application Ser. No. 60/062,922, filed Oct. 20, 1997, and to U.S. patent application Ser. No. 60/076,985, filed Mar. 5, 1998.

TECHNICAL FIELD

The invention relates to methods and apparatus used for optical diagnosis of tissue abnormalities, and more particularly to detection of tissue abnormalities by fluorescence spectroscopy of normal and neoplastic tissue, particularly epithelium.

BACKGROUND

Among the many forms of cancer, cervical cancer is the second most common malignancy in women worldwide, exceeded only by breast cancer. In the United States, cervical cancer is the third most common neoplasm of the female genital tract. In 1994, 15,000 new cases of invasive cervical cancer and 55,000 cases of carcinoma in situ (CIS) were reported in the U.S. In the same year, an estimated 4,600 deaths occurred in the United States alone from cervical cancer. Recently, the incidence of pre-invasive squamous carcinoma of the cervix has risen dramatically, especially among young women. Women under the age of 35 years account for up to 24.5% of patients with invasive cervical cancer, and the incidence is continuing to increase for women in this age group. It has been estimated that the mortality of cervical cancer may rise by 20% in the next decade unless further improvements are made in detection techniques.

Early detection of cervical cancer, or of the pre-cancerous state called squamous intraepithelial lesion (SIL), can reduce the mortality associated with this disease. Currently, a Pap smear is used to screen for CIS and cervical cancer in the general female population. In a Pap smear, a large number of cells, obtained by scraping the cervical epithelium, are smeared onto a slide, which is then fixed and stained for cytologic examination. The Pap smear is unable to achieve a concurrently high sensitivity and high specificity due to both sampling and reading errors. For example, estimates of the sensitivity and specificity of Pap smears screening have ranged from 11–99% and 14–97%, respectively.

Furthermore, reading Pap smears is extremely labor intensive and requires highly trained professionals. A patient with an abnormal Pap smear indicating the presence of SIL is followed up by a diagnostic procedure called colposcopy, which involves colposcopic examination, biopsy and histologic confirmation of the clinical diagnosis. Colposcopy requires extensive training and its accuracy for diagnosis is variable and limited, even in expert hands. Moreover, diagnosis is not immediate. Thus, it would be desirable to provide a way to reduce cervical cancer rates by improving the methods for early detection. It also would be desirable to provide a diagnostic method that could improve the level of specificity and sensitivity, reduce the required skill level of the practitioner interpreting the results, and shorten the time that it takes to arrive at a diagnosis.

In vivo fluorescence spectroscopy is a technique which has the capability to quickly, non-invasively and quantitatively probe the biochemical and morphological changes that occur as tissue becomes neoplastic. The measured spectral information can be correlated to tissue histopathology to develop clinically effective screening and diagnostic techniques. By using automated data analysis techniques, there is the potential for an automated, fast, noninvasive and accurate pre-cancer screening and diagnosis system that can be used by non-experts.

Screening and diagnostic techniques for human tissue, and cervical pre-cancer tissue in particular, based on induced fluorescence spectroscopy have been developed relatively recently; see, for example, the following U.S. patents and patent applications, the teachings of which are hereby incorporated by reference: U.S. Pat. No. 5,699,795 to Richard-Kortums et al., Optical Probe for the Detection of Cervical Neoplasia Using Fluorescence Spectroscopy and Apparatus Incorporating Same; U.S. Pat. No. 5,697,373 to Richard-Kortums et al., Optical Method and Apparatus for the Diagnosis of Cervical Precancers Using Raman and Fluorescence Spectroscopies; U.S. Pat. No. 5,623,932 to Ramanujam et al., Diagnosis of Dysplasia Using Laser Induced Fluorescence; U.S. Pat. No. 5,612,540 to Richard-Kortums et al., Optical Method for the Detection of Cervical Neoplasias Using Fluorescence Spectroscopy; U.S. Pat. No. 5,562,100 to Kittrell et al., Method for Laser Induced Fluorescence of Tissue; U.S. Pat. No. 5,697,373 to Richard-Kortums et al., Optical Method and Apparatus for the Diagnosis of Cervical Precancers Using Raman and Fluorescence Spectroscopies; U.S. Pat. No. 5,612,540 to Richard-Kortums et al., Optical Method for the Detection of Cervical Neoplasias Using Fluorescence Spectroscopy; U.S. Pat. No. 5,421,339 to Richard-Kortums et al., Diagnosis of Dysplasia Using Laser Induced Fluorescence; U.S. Pat. No. 5,419,323 to Kittrell et al., Method for Laser Induced Fluorescence of Tissue; U.S. Pat. No. 5,345,941 to Rava et al., Contour Mapping of Spectral Diagnostics; U.S. Pat. No. 5,201,318 to Rava et al., Contour Mapping of Spectral Diagnostics; Ser. No. 467,993, Near-Infrared Raman Spectroscopy for In vitro and in vivo Detection of Cervical Precancers; Ser. No. 693,471, Method and Apparatus for the characterization of Tissue of Epithelial Lined Viscus; and Ser. No. 672,623, Spectroscopy Probe for In vivo Measurement of Raman Signals.

A problem with most optical and spectroscopic measurement systems and techniques is obtaining suitable signals indicative of the property to be measured. Contrast agents have been commonly applied to tissue in vitro and in vivo to enhance the optical return signal of illuminated tissue and thus aid in the extraction of diagnostically useful information from the sample. For example, techniques are commonly used to highlight cellular structures when using light microscopy to examine tissue samples. On a more gross level, sensitive differentiation between normal tissue and neoplasia in various tissue sites has been recently demonstrated through the use of 5-aminolevulinic acid induced protoporphyrin IX fluorescence.

Acetic acid is routinely used during colposcopy, a procedure involving examination of the cervix in situ with a low power microscope, to enhance differences between normal and diseased regions of the cervical epithelium. Areas which may develop into cervical cancer undergo a transient whitening (acetowhitening) visible to the naked eye. While the mechanism behind this phenomenon is not yet fully understood, it is commonly agreed that the higher nuclear density present in abnormal epithelium is a significant factor.

The inventors have determined that it would be desirable to provide a technique for the automatic spectroscopic detection of cervical pre-cancer that provides greater sensitivity and selectivity than prior techniques by enhancing the optical return signal in a manner that is indicative of abnormal tissue. The present invention provides such a technique.

SUMMARY

The invention includes use of acetic acid as a signal enhancing contrast agent during fluorescence spectroscopy of normal and neoplastic tissue, particularly epithelium. More particularly, in one aspect, the invention includes a method of detecting tissue abnormality in a diagnostic tissue sample in a patient, comprising the steps of obtaining a first fluorescence intensity spectrum from the diagnostic tissue sample; thereafter, applying acetic acid to the diagnostic tissue sample in sufficient concentration to alter the response of such diagnostic tissue sample to electromagnetic radiation for at least an effective period of time; during the effective period of time, obtaining a second fluorescence intensity spectrum from the diagnostic tissue sample; determining a parameter indicative of a change between the first and second fluorescence emission intensity spectra; and analyzing the determined parameter to determine a probability that the diagnostic tissue sample is normal or abnormal.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is a graph showing a mapping of peak emission wavelength shift due to acetic acid from a normal site and an abnormal site.

FIGS. 3(a) and 3(b) are line graphs showing, respectively, the unnormalized and the normalized data of the significance level a for the t-test between categories.

FIGS. 5(a) and 5(b) are line graphs showing, respectively, the unnormalized ($\alpha=0.07$) and the normalized ($\alpha=0.05$) data of significant emission wavelengths vs. percentage of patients for each category.

DETAILED DESCRIPTION

Confirmation of Effect

The invention includes use of acetic acid as a signal enhancing contrast agent during fluorescence spectroscopy of normal and neoplastic tissue, particularly epithelium. To confirm the enhanced optical return signal from use of acetic acid, we measured fluorescence spectra of the cervix in vivo from 100 patients referred for colposcopy and treatment due to the presence of cervical precancer. The emission spectra, collected at 337 nm excitation, were acquired using a multi-pixel fiber optic probe designed to collect 31 spatially resolved spectra with 2 mm resolution. The spectra were recorded with an imaging spectrograph onto an imaging array (e.g., a CCD integrated circuit imaging array). Spectra were acquired by placing the probe in each of four quadrants of the cervix both before and after acetic acid (preferably a 3% solution) was applied to the cervix for colposcopy. The patients were then treated by a conventional loop electro-surgical excision procedure to remove the precancerous region of tissue. We identified differences between pre-and post-acetic acid spectra and correlated these differences with the colposcopic impression and pathologic diagnosis.

An example of a spectroscopic system suitable for use in practicing the present invention is described in U.S. Pat. No. 5,697,373. This system includes a laser, an optical fiber probe, and an optical multi-channel analyzer utilized to record fluorescence spectra from the intact cervix at colposcopy.

Figure 1A:
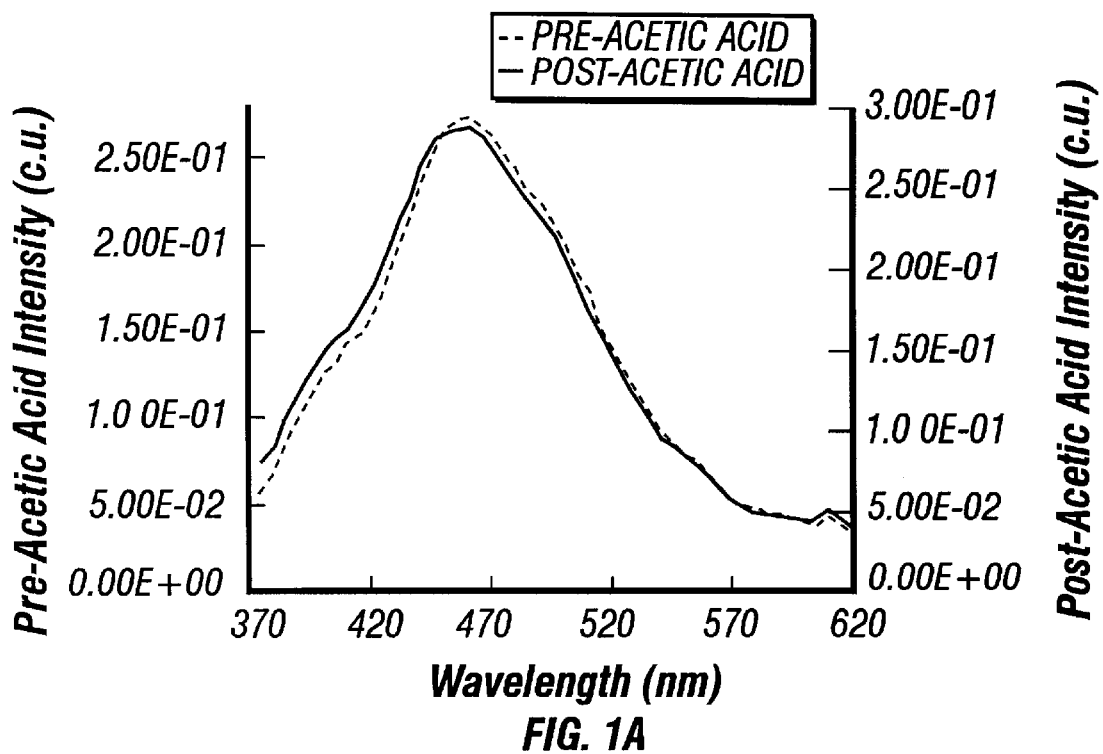
FIG. 1(a) is a graph of fluorescence spectra pre- and post-acetic acid from a pathologically normal site.
Figure 1B:
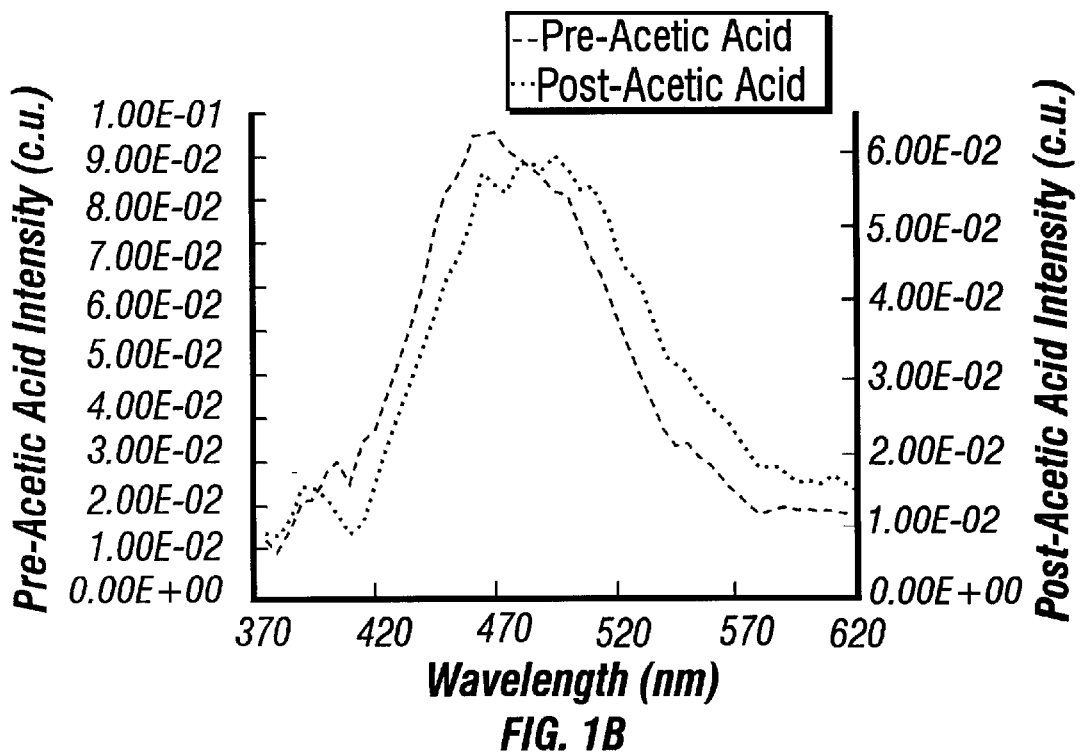
FIG. 1(b) is a graph of fluorescence spectra pre- and post-acetic acid from a pathologically abnormal site.

FIG. 1(a) is a graph of fluorescence spectra pre- and post-acetic acid from a pathologically normal site. FIG. 1(b) is a graph of fluorescence spectra pre- and post-acetic acid from a pathologically abnormal site. At the normal site, the addition of acetic acid has little effect on the peak emission wavelength of the spectrum. However, following addition of acetic acid, the peak of the spectrum from the abnormal site is red-shifted. FIGS. 1(a) and 1(b) illustrate spectra from a single pixel of the multi-pixel probe used to map fluorescence of a 1 cm diameter region of the cervical epithelium.

FIG. 2 is a graph showing a mapping of peak emission wavelength shift due to acetic acid from a normal site and an abnormal site. In FIG. 2, the shift in the fluorescence peak emission wavelength post-acetic acid is plotted as a function of pixel location for two placements of the probe, one at a normal site, (a), and one at a site containing a high-grade precancer (b). At the abnormal site (b), the average shift is greater than that of the normal site (a), illustrating that spectral shifts occur consistently throughout normal or abnormal regions of the cervix. Previous studies (Ramanujam, N., et al., "In vivo diagnosis of cervical intraepithelial neoplasia using 337-nm excited laser induced fluorescence", Proc. Natl. Acad. Sc. USA 1994, 91:10193–10197) have obtained 337 nm excited fluorescence spectra only post-acetic acid and have shown that the spectra of precancerous tissue exhibit a red shift relative to the spectra of normal tissue. These results are consistent with those presented here, and indicate that acetic acid may play an important role in the ability of 337 nm excited fluorescence to discriminate normal and abnormal cervical epithelium.

The effect of acetic acid as a signal enhancing contrast agent during fluorescence spectroscopy can be shown by statistical analysis. Spectra from a number of patients was obtained as described above, with data taken from four quadrants of the cervix. All data was analyzed per patient. Because of probe placement and pathology methods, all spectra before or after application of acetic acid from each quadrant was classified as normal or abnormal. For categories of spectra were established:

Normal/Before acetic acid (NB)

Abnormal/Before acetic acid (AB)

Normal/After acetic acid (NA)

Abnormal/After acetic acid (AA)

A statistical method (t-test) was used to compare fluorescence intensities at each emission wavelength between categories:

NB vs. AB

NB vs. NA

NA vs. AA

AB vs. AB

The comparisons were made for both normalized (to peak value of 1) and unnormalized spectra.

Figure 4B:
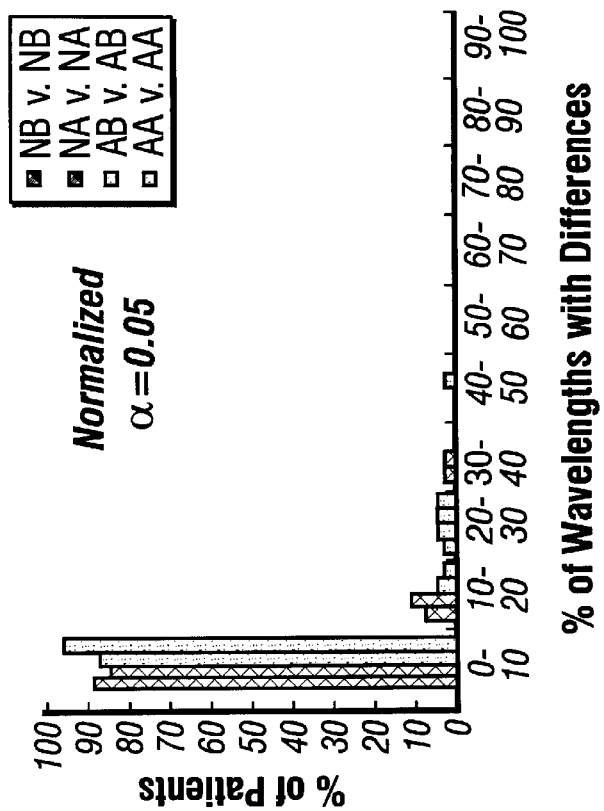
FIGS. 4(a) and 4(b) are bar graphs showing, respectively, the unnormalized ($\alpha=0.07$) and the normalized ($\alpha=0.05$) data of the percentage of wavelengths with differences vs. percentage of patients for each category.
Figure 4A:
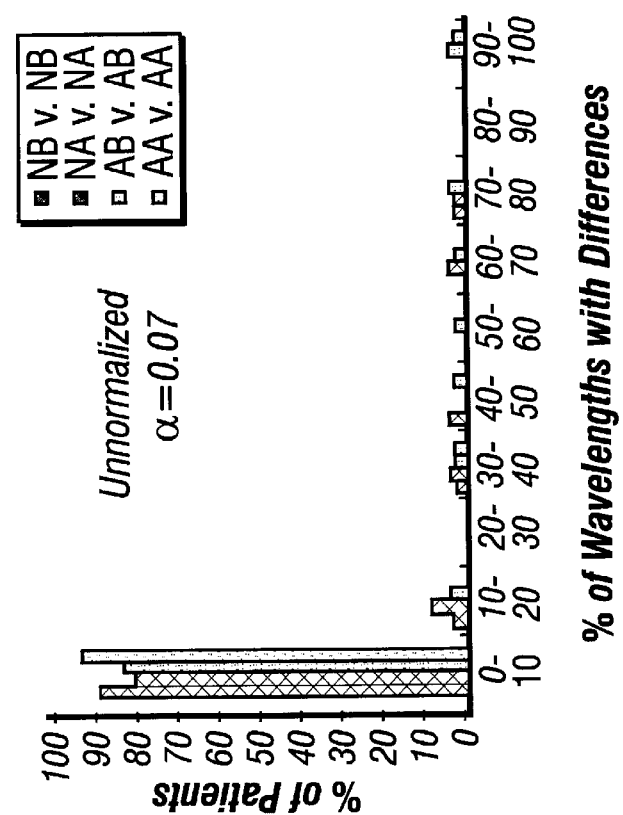

A significance level (α) for the t-test between categories was established as follows: For each patient, the spectra from a single category were divided into to random groups. The mean spectrum for each group was determined. The largest value of α was then determined where the two mean spectra appear to be essentially the same (differences <10% of emission wavelengths) for at least 80% of patients. FIGS. 3(a) and 3(b) are line graphs showing, respectively, the unnormalized and the normalized data of the significance level a for the t-test between categories. FIGS. 4(a) and 4(b) are bar graphs showing, respectively, the unnormalized (α=0.07) and the normalized (α=0.05) data of the percentage of wavelengths with differences vs. percentage of patients for each category.

Figures 5A, 5B:
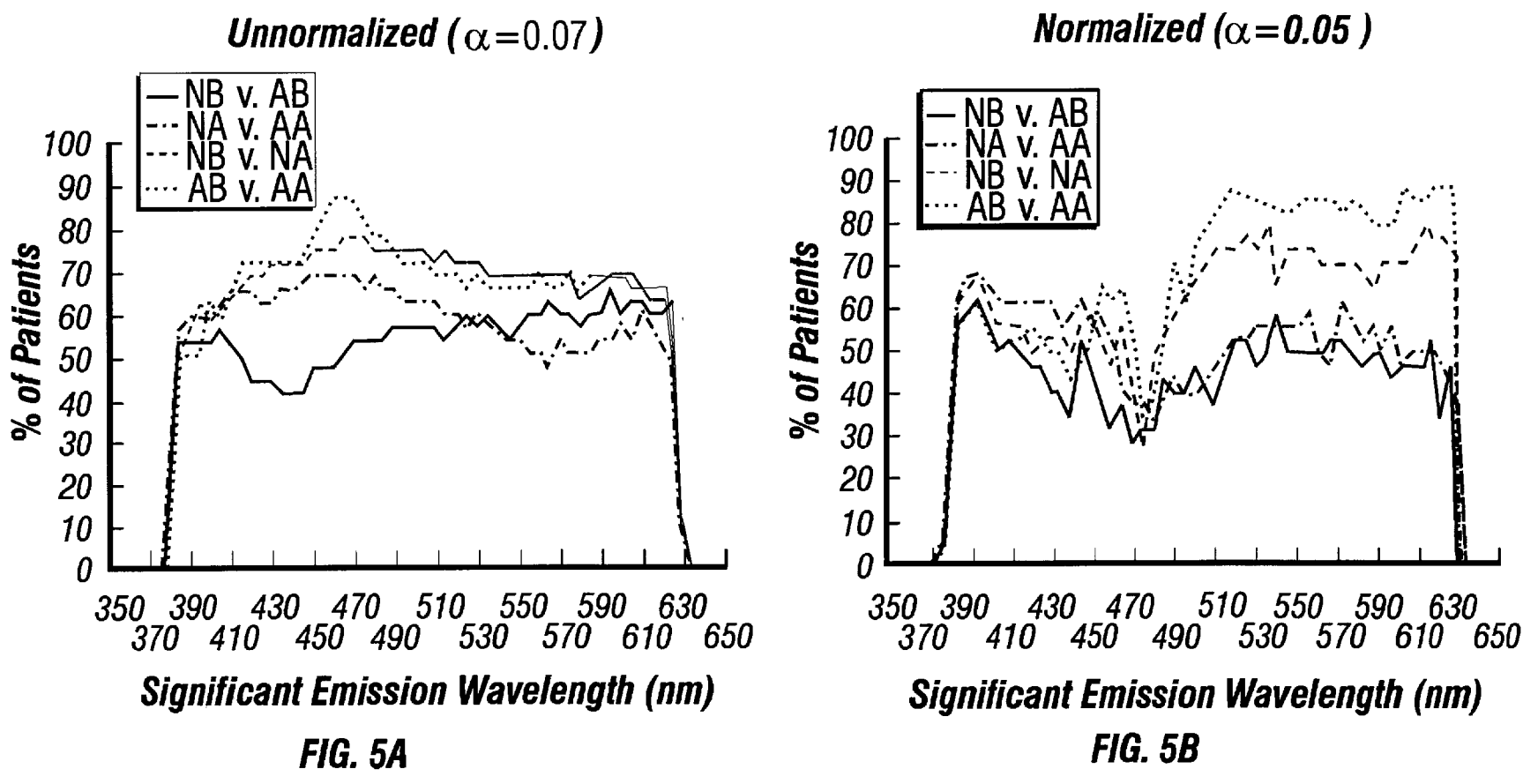

The amount and spectral dependence of significant differences between categories was then determined. A t-test was performed at each emission wavelength to determine if the distributions of intensities for two categories were significantly different. FIGS. 5(a) and 5(b) are line graphs showing, respectively, the unnormalized (α=0.07) and the normalized (α=0.05) data of significant emission wavelengths vs. percentage of patients for each category.

Figure 6:
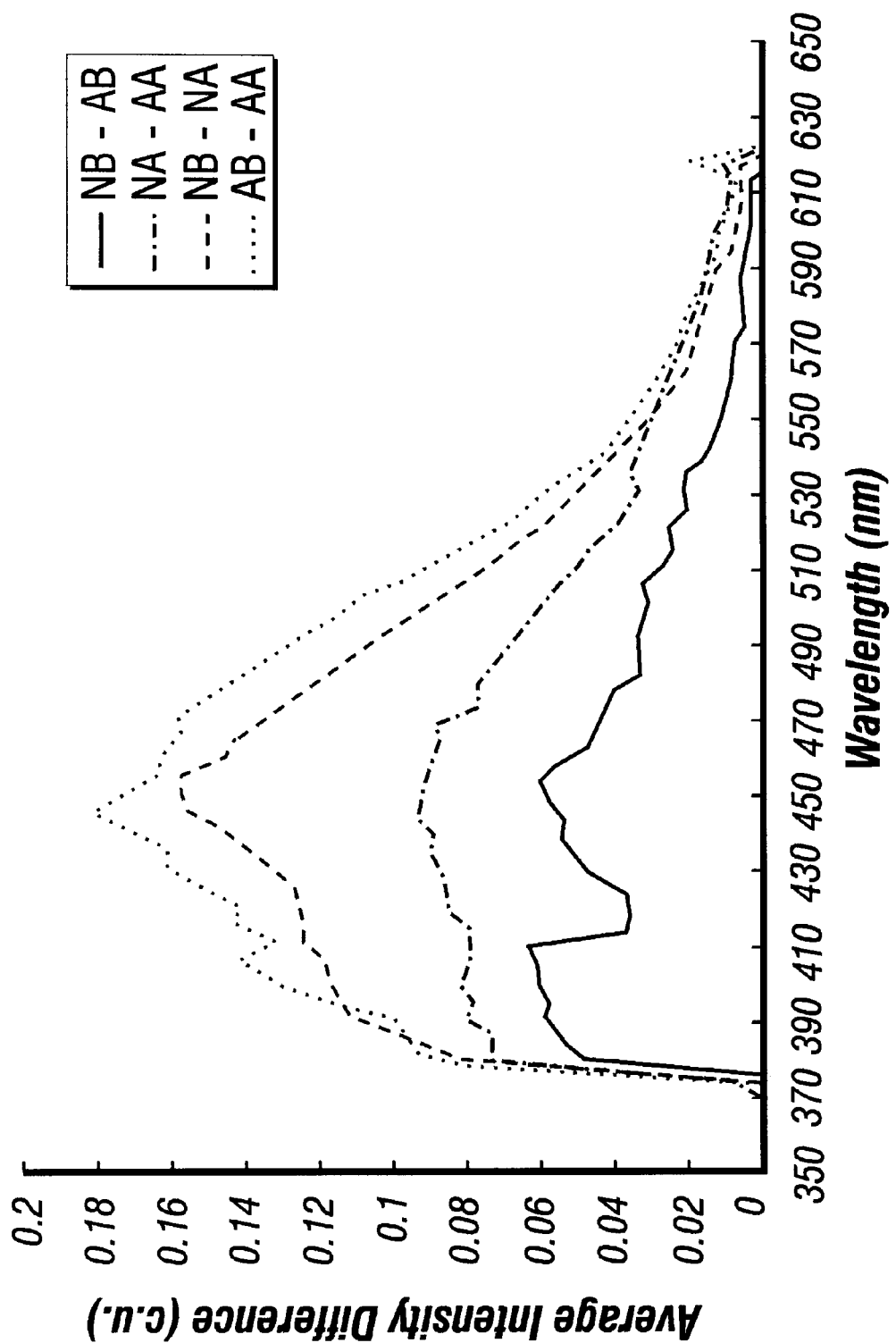
FIG. 6 is a line graph showing the average difference in intensities (using unnormalized spectra) between categories over all patients.

FIG. 6 is a line graph showing the average difference in intensities (using unnormalized spectra) between categories over all patients. Comparing lines NB-AB and NA-AA, application of acetic acid increases the signal between normal and abnormal tissue at almost all wavelengths compared to data from tissue without acetic acid. Comparing lines NB-NA and AB-AA, application of acetic acid has a greater effect on abnormal tissue than on normal tissue at almost all wavelengths.

Preferred Methods

Having demonstrated that acetic acid can produce measurable differences in optical spectra and images which may be diagnostically useful, the following is the preferred method of embodying this discovery in practice:

(1) Obtain a first fluorescence emission intensity spectrum from the diagnostic tissue sample, resulting from illuminating the diagnostic tissue sample with excitation electromagnetic radiation. For in vivo applications, the tissue is preferably epithelium. For detection of cervical abnormalities, the tissue is preferably epithelium from the cervix. Preferred excitation wavelengths are about 380 nm, 337 nm, and 460 nm.

(2) Thereafter, applying acetic acid to the diagnostic tissue sample in sufficient concentration to alter the response of the diagnostic tissue sample to excitation electromagnetic radiation for at least an effective period of time. Typical concentrations of acetic acid are 3%–6%, but any medically safe concentration that produces the desired alteration in response is suitable.

(3) During the effective period of time, obtaining a second fluorescence intensity spectrum from the diagnostic tissue sample. Again, preferred excitation wavelengths are about 380 nm, 337 nm, and 460 nm. In any event, the preferred embodiment utilizes substantially identical excitation wavelengths for both the first and second fluorescence emission intensity spectra.

(4) A parameter indicative of a change between the first and second fluorescence intensity spectra is then determined. It has been found that application of acetic acid results in a change in measured intensity between the first and second fluorescence emission intensity spectra. Acetic acid causes an overall reduction in detected fluorescence intensity, but with a greater affect on abnormal tissue than on normal tissue. It has also been found that application of acetic acid results in a change in measured red shift between the first and second fluorescence emission intensity spectra, and more particularly a red shift in the peak emission wavelength. Thus, acetic acid enhances differences in fluorescence intensity and line shape between normal and abnormal tissue. A working hypothesis for the affect of acetic acid on tissue is that acetic acid causes less excitation light (and less emission light) to penetrate "directly" through epithelium due to increased scattering of light. If is further believed that the contribution to emissions by at least certain fluorophores (e.g., NADH, FAD) and absorbers (e.g., hemoglobin) in the stroma beneath the epithelium is diminished.

(5) Once a desired indicator parameter is determined, the indicator parameter can be analyzed to calculate a probability that the diagnostic tissue sample is normal or abnormal. One method of analysis is simply to compare the indicator parameter to an empirically determined threshold value. If the indicator parameter exceeds the threshold value, an indication can be made of possible tissue abnormality in the diagnostic tissue sample. However, other methods of analysis can be applied that can utilize the fact that application of acetic acid provides an enhanced fluorescence spectra signal between normal and abnormal tissue.

A number of embodiments of the present invention have been described. Nevertheless, it will be understood that various modifications may be made without departing from the spirit and scope of the invention. For example, other apparatus than that described can be used with the inventive method. Accordingly, other embodiments are within the scope of the following claims.

What is claimed is:

1. A method of detecting tissue abnormality in a diagnostic tissue sample in a patient, comprising:

(a) obtaining a first fluorescence emission intensity spectrum from the diagnostic tissue sample;

(b) thereafter, applying acetic acid to the diagnostic tissue sample in sufficient concentration to alter the response of such diagnostic tissue sample to excitation electromagnetic radiation, said acetic acid being applied for a selected period of time;

(c) obtaining a second fluorescence emission intensity spectrum from the diagnostic tissue sample during said selected period of time;

(d) determining a parameter indicative of a change between the first and second fluorescence emission intensity spectra, where said parameter is indicative of hemoglobin absorption; and (e) analyzing the determined parameter to determine a probability that the diagnostic tissue sample is normal or abnormal.

2. The method of claim 1, wherein the step of analyzing the determined parameter to determine a probability that the diagnostic tissue sample is normal or abnormal includes the step of comparing the determined parameter to a threshold value to indicate tissue abnormality in the diagnostic tissue sample if the determined parameter exceeds the threshold value.

3. A method of detecting tissue abnormality, comprising:

(a) illuminating a diagnostic tissue sample with excitation electromagnetic radiation;

(b) detecting a first fluorescence emission intensity spectrum from the diagnostic tissue sample resulting from such illuminating;

(c) thereafter, exposing the diagnostic tissue sample to acetic acid in sufficient concentration to have an effect of detectably altering the response of such diagnostic tissue sample to excitation electromagnetic radiation, where said acetic acid is applied to the tissue sample for a selected period of time;

(d) illuminating the diagnostic tissue sample with excitation electromagnetic radiation during said selected period of time;

(e) detecting a second fluorescence emission intensity spectrum from the diagnostic tissue sample resulting from such further illuminating;

(f) determining a parameter indicative of a change between the first and second fluorescence emission intensity spectra, where said parameter is indicative of hemoglobin absorption; and (g) comparing the determined parameter to a threshold value to indicate tissue abnormality in the diagnostic tissue sample if the determined parameter exceeds the threshold value.

4. The method of claim 3, wherein the electromagnetic radiation in steps (a) and (d) are essentially identical wavelengths.

5. The method of claim 3, wherein the electromagnetic radiation used in steps (a) and (d) has a wavelength of about 380 nm.

6. The method of claim 3, wherein the electromagnetic radiation used in steps (a) and (d) has a wavelength of about 337 nm.

7. The method of claim 3, wherein the electromagnetic radiation used in steps (a) and (d) has a wavelength of about 460 nm.

8. The method of claims 1 or 3, performed with a cervical tissue sample as the diagnostic tissue sample.

9. The method of claims 1 or 3, wherein the diagnostic tissue sample is in vivo.

10. A method of detecting tissue abnormality in a diagnostic tissue sample in a patient, comprising:

(a) obtaining a first fluorescence emission intensity spectrum from the diagnostic tissue sample;

(b) thereafter, applying acetic acid to the diagnostic tissue sample in sufficient concentration to alter the response of such diagnostic tissue sample to excitation electromagnetic radiation, said acetic acid being applied for a selected period of time;

(c) obtaining a second fluorescence emission intensity spectrum from the diagnostic tissue sample during said selected period of time;

(d) determining a parameter indicative of a change between the first and second fluorescence emission intensity spectra, where said parameter is indicative of red shift; and (e) analyzing the determined parameter to determine a probability that the diagnostic tissue sample is normal or abnormal.

11. A method of detecting tissue abnormality, comprising:

(a) illuminating a diagnostic tissue sample with excitation electromagnetic radiation;

(b) detecting a first fluorescence emission intensity spectrum from the diagnostic tissue sample resulting from such illuminating;

(c) thereafter, exposing the diagnostic tissue sample to acetic acid in sufficient concentration to have an effect of detectably altering the response of such diagnostic tissue sample to excitation electromagnetic radiation, where said acetic acid is applied to the tissue sample for a selected period of time;

(d) illuminating the diagnostic tissue sample with excitation electromagnetic radiation during said selected period of time;

(e) detecting a second fluorescence emission intensity spectrum from the diagnostic tissue sample resulting from such further illuminating;

(f) determining a parameter indicative of a change between the first and second fluorescence emission intensity spectra, where said parameter is indicative of red shift; and (g) comparing the determined parameter to a threshold value to indicate tissue abnormality in the diagnostic tissue sample if the determined parameter exceeds the threshold value.

12. The method of claim 10, wherein the parameter is indicative of a shift in peak emission wavelength.

13. The method of claim 11, wherein the parameter is indicative of a shift in peak emission wavelength.

* * * * *